United States Patent
Rollat-Corvol et al.

(12)

(10) Patent No.: US 6,432,385 B1
(45) Date of Patent: Aug. 13, 2002

(54) COSMETIC COMPOSITIONS COMPRISING AT LEAST ONE FILM-FORMING POLYMER

(75) Inventors: Isabelle Rollat-Corvol, Paris; Henri Samain, Bievres, both of (FR)

(73) Assignee: L'Oreal, S.A., Paris (FR)

( * ) Notice: Subject to any disclaimer, the term of this patent is extended or adjusted under 35 U.S.C. 154(b) by 0 days.

(21) Appl. No.: 09/714,173

(22) Filed: Nov. 17, 2000

(30) Foreign Application Priority Data

Nov. 19, 1999 (FR) .............................. 99 14588

(51) Int. Cl.$^7$ ............................ A16K 7/00; A16K 7/06; A16K 7/11; A16K 31/74; A16K 31/78
(52) U.S. Cl. ........................... 424/45; 424/47; 424/484; 424/70.16; 424/78.03; 424/401; 424/DIG. 2; 514/772.3; 514/944
(58) Field of Search ................................ 424/45, 70.16, 424/78.03, 484, 47, DIG. 1, DIG. 2; 514/772.3, 944

(56) References Cited

U.S. PATENT DOCUMENTS

| | | | |
|---|---|---|---|
| 5,297,566 A | | 3/1994 | Firstenberg et al. |
| 5,753,215 A | * | 5/1998 | Mougin et al. .......... 424/70.11 |
| 5,817,304 A | * | 10/1998 | Mondet et al. .......... 424/78.03 |
| 5,965,116 A | * | 10/1999 | Mondet et al. .......... 424/70.16 |

FOREIGN PATENT DOCUMENTS

| | | |
|---|---|---|
| EP | 0 418 676 | 3/1991 |
| EP | 0 524 346 | 1/1993 |
| EP | 0 845 257 | 6/1998 |
| FR | 2 786 391 | 6/2000 |
| WO | WO 97/02809 | 1/1997 |
| WO | WO 99/63954 | 12/1999 |

OTHER PUBLICATIONS

"Avalure™ Film Forming Polymers for Personal Care Applications", Polymers for Personal Care, BF Goodrich, TDS–248, Apr. 28, 1997, pp. 1–4.
Copending Application by Isabelle Rollat–Corvol and Pascale Cothias, entitled Cosmetic Compositions Comprising At Least One Polymer with Specific Characteristics and At Least One Thickening Polymer, filed Nov. 17, 2000.
English language Derwent Abstract of EP 0 845 257.
English language Derwent Abstract of FR 2 786 391.

* cited by examiner

*Primary Examiner*—Fredrick Krass
*Assistant Examiner*—Clinton Ostrup
(74) *Attorney, Agent, or Firm*—Finnegan, Henderson Farabow, Garrett & Dunner, L.L.P.

(57) ABSTRACT

Cosmetic compositions comprising at least one film-forming polymer, in a cosmetically acceptable medium, wherein said at least one film-forming polymer has, at the polymer concentration of the composition, a mechanical profile, measured in an aqueous-alcoholic medium comprising 20% by volume of ethanol, defined by at least:

(i) an attachment angle α of greater than 47°, and
(ii) if α is greater than or equal to 90°, a maximum detachment force $F_{max} < 5$ newtons.

16 Claims, No Drawings

COSMETIC COMPOSITIONS COMPRISING AT LEAST ONE FILM-FORMING POLYMER

The present invention relates to cosmetic compositions comprising at least one film-forming polymer, wherein said at least one film-forming polymer has a specific mechanical profile. The invention is also directed toward a cosmetic process comprising the application of this composition, and a cosmetic process comprising application of such compositions for at least fixing or holding the shape of the hairstyle.

The compositions in accordance with the invention can be applied to keratin materials such as the skin, the nails, the lips, the hair, the eyebrows and the eyelashes.

For the purposes of the present invention, the expression "styling compositions" means compositions intended to at least fix or hold the shape of the hairstyle.

Cosmetic compositions, for instance styling compositions, which contain polymers dissolved or dispersed in a solvent, optionally in the presence of additives, are already known. The application of such compositions to the hair can be performed with the aid of a spray and by hand. In general, after evaporation of the solvent, generally water or alcohol, a material which produces the styling effect can remain on the hair.

The starting materials constituting the styling composition are usually chosen such that the material resulting from the drying of the composition on the hair tends to be solid, if not rigid and at least soft.

When the hair dries without any mechanical assistance, for example naturally, welds can form between the hairs. As a result, it is possible to hold the hairstyle in a desired shape. The presence of the welds, serving as juncture points, can be felt by passing a hand through the hair.

If the person combs or disentangles his hair, the welds can break and the shape of the hairstyle may no longer be held. Likewise, when hair is subjected to external mechanical forces, for example if the person himself makes very sudden movements or if he is caught in a gust of wind, a similar result may occur.

If, after having applied a styling product, the hair is, for example, blow-dried, rather than welds being formed between the hairs, a continuous coating which envelopes the hair may be formed. In this case, the more moderate styling effect may disappear faster, such as with the first gust of wind or the first constraint suffered.

Another possible drawback of cosmetic products known previously, in particular hair care products, is that such products can occasionally impair keratin fibers, such as the hair, tending to make the fibers dry and brittle and tending to cause the fibers to lose their natural appearance.

There is thus a need to find cosmetic compositions that fix keratin fibers, in particular the hair, in a more lasting manner than the compositions known previously and/or that give the keratin fibers satisfactory cosmetic properties.

The inventors have discovered, surprisingly and unexpectedly, that it is possible to provide cosmetic compositions which satisfy at least one of the requirements expressed above, by judiciously selecting the polymers used to prepare such cosmetic compositions.

One subject of the invention is a cosmetic composition comprising at least one film-forming polymer, in a cosmetically acceptable medium, wherein said at least one film-forming polymer has, at the polymer concentration of the composition, a mechanical profile, measured in an aqueous-alcoholic medium comprising 20% by volume of ethanol, defined by at least:
(i) an attachment angle α of greater than 47°, and
(ii) if a is greater than or equal to 90°, a maximum detachment force $F_{max}$<5 newtons.

One embodiment of the invention has a maximum detachment force of less than 2 newtons, when a is greater than or equal to 90°.

Another subject of the present invention concerns a cosmetic process comprising the use of this composition.

Yet another subject of the present invention concerns the use of a cosmetic composition comprising at least one film-forming polymer, in a cosmetically acceptable medium, wherein said at least one film-forming polymer has, at the polymer concentration of the composition, a mechanical profile, measured in an aqueous-alcoholic medium comprising 20% by volume of ethanol, defined by at least:
(i) an attachment angle α of greater than 47°, and
(ii) if a is greater than or equal to 90°, a maximum detachment force $F_{max}$<5 newtons, with, in a specific embodiment, for (ii), $F_{max}$<2 newtons.

The at least one film-forming polymer particularly targeted by the present invention is the polyurethane PA Marin UA 200 sold by Sanyo. The present invention is also directed toward, combinations, in specific concentrations, of the polymer comprising polyacrylic acid units, Avalure AC315, sold by Goodrich, either with the vinylcaprolactam/PVP/dimethylaminoethyl methacrylate copolymer sold by ISP under the name Gaffix VC 713, or with the grafted silicone copolymer Polysilicone 8 sold under the name VS80 by 3M.

The term "$F_{max}$" means the maximum tensile force, measured using an extensometer, required to detach areas of 0.95 cm² respectively of two rigid, inert, non-absorbing supports (A) and (B) placed opposite each other; wherein said areas are coated beforehand with said composition of solids concentration c, at a rate of 4/c mg/cm², dried for 48 hours at 22° C. under a relative humidity of 50% and then subjected for 20 seconds to a compression of 3 newtons and finally subjected for 60 seconds to traction at a speed of 10 mm/minute; c is the solids concentration in the composition (in grams per gram of composition).

Supports (A) and (B), for example, can be chosen from polyethylene, polypropylene, metal alloy and glass.

The attachment angle α is determined by following the protocol described below.

A first film of 243 cm² is prepared by depositing in a Petri dish an amount of composition such that, after drying, 0.8 g of material remains in the dish. Specifically, the composition is deposited in the Petri dish and is left to dry for 48 hours at room temperature and 50% relative humidity. The film obtained is called $F_1$.

A coaxial assembly formed from two cylinders, a glass disk forming a pellet and a film $F_2$ is prepared.

A first cylinder measuring 0.6 cm in height and 2.2 cm in diameter is used. A pellet measuring 1.1 cm in diameter and 0.3 cm in height is placed on one of the ends of this cylinder.

A second cylinder measuring 2 cm in height and 0.5 cm in diameter is placed on the other end of this first cylinder.

The total mass of the assembly is 13.4 g. The center of gravity is on the transverse axis, 0.4 cm from the outer surface of the pellet.

A second film $F_2$ is prepared by depositing, on the outer face of the pellet, an amount of composition such that, after drying, the pellet is covered with 4 mg of material. Drying is carried out while maintaining the assembly for 48 hours at room temperature and at a relative humidity of 50%.

The film $F_1$ is fixed to a horizontal plane. The assembly is placed on the film $F_1$ in a removable manner, the film $F_2$ coming completely into contact with the film $F_1$.

The horizontal plane is inclined at a speed of 11 degrees per second, until the assembly slips. The attachment angle $\alpha_i$ measured is the angle between the film $F_1$ and the horizontal at the moment when the surface of the film $F_2$ begins to move relative to the surface of the film $F_1$.

The experiment is repeated four times in succession with the same pellet and the average of the angles $\alpha_i$ is calculated for one pellet. The protocol is repeated with 4 different pellets, and the average of the attachment angles $\alpha_i$ measured is calculated, which gives the attachment angle $\alpha$.

In accordance with the invention, the angle $\alpha$ is preferably greater than 50°.

In the compositions in accordance with the invention, generally, the at least one film-forming polymer is present in an amount ranging from 0.05% to 20% by weight, such as from 0.1% to 15% by weight, and further such as from 0.25% to 10% by weight, relative to the total weight of the composition.

The cosmetically acceptable medium can comprise a medium chosen from water, at least one cosmetically acceptable solvent, such as alcohols, and water and at least one cosmetically acceptable solvent, wherein such solvents are chosen from $C_1$–$C_4$ alcohols.

Among these alcohols which may be mentioned are ethanol and isopropanol, and in particular, ethanol.

The composition of the invention can also contain at least one additive chosen from thickeners, anionic, nonionic, cationic and amphoteric surfactants, fragrances, preserving agents, sunscreens, proteins, vitamins, provitamins, non-fixing anionic, cationic, nonionic and amphoteric polymers, mineral, plant and synthetic oils, waxes, ceramides, pseudoceramides and any other additive conventionally used in cosmetic compositions intended to be applied to the hair.

One skilled in the art should take care to select the optional compound(s) to add to the composition according to the invention such that the properties associated with the composition in accordance with the invention are not substantially adversely affected by the addition envisaged.

The compositions in accordance with the present invention can be packaged in various forms, including pump-dispenser bottles and aerosol containers comprising a recipient as well as a means for distributing the composition, in order to apply the composition in vaporized form or in the form of a mousse. Such packaging forms are indicated, for example, when it is desired to obtain a spray, a lacquer or a mousse for fixing or treating the hair. The compositions in accordance with the invention can also be in the form of creams, gels, emulsions, lotions or waxes.

When the composition according to the invention is packaged in aerosol form in order to obtain a lacquer or a mousse, it comprises at least one propellant which can be chosen from volatile hydrocarbons such as n-butane, propane, isobutane, pentane and chlorohydrocarbons and fluorohydrocarbons. Carbon dioxide, nitrous oxide, dimethyl ether (DME), nitrogen and compressed air can also be used as propellant. Mixtures of propellants can also be used. Dimethyl ether is preferably used.

Generally, the propellant is present in an amount ranging from 5% to 90%, such as from 10% to 60% by weight relative to the total weight of the composition in the aerosol device.

The compositions in accordance with the invention can be applied to wet or dry hair.

The invention may be understood more clearly with the aid of the non-limiting examples which follow, which constitute advantageous embodiments of the compositions in accordance with the invention.

EXAMPLE

The following compositions in accordance with the invention were prepared.

| Composition 1 | |
|---|---|
| Avalure AC 315 (Goodrich) | 5 g (active material) |
| Gaffix VC 713 (I.S.P.) | 2 g (active material) |
| Water qs | 100 g |
| Composition 2 | |
| PA Marin UA-200 (Sanyo) | 5 g (active material) |
| Water qs | 100 g |

The attachment effect and the bonding effect of the polymer of composition 2 or of the mixture of polymers of composition 1 were measured by evaluating $F_{max}$ and $\alpha_i$ respectively. The results are collated in Table 1 below.

TABLE 1

| Composition | Attachment angle $\alpha$ (°) | Maximum Attachment Force $F_{max}$ (newtons) |
|---|---|---|
| 1 | 50° | 0.3 |
| 2 | 90°* | 4.2 |

*: at 90°, the assembly did not slip. The experiment was stopped.

The two compositions 1 and 2 in accordance with the invention gave natural hair, after they were applied, a very good natural, non-sticky and very long-lasting hold.

What is claimed is:

1. A cosmetic composition comprising at least one film-forming polymer, in a cosmetically acceptable medium, wherein said at least one film-forming polymer has a mechanical profile, measured in an aqueous-alcoholic medium comprising 20% by volume, relative to the total volume of said aqueous-alcoholic medium, of ethanol, defined by at least:
    (i) an attachment angle $\alpha$ of greater than 47°, and
    (ii) if $\alpha$ is greater than or equal to 90°, a maximum detachment force $F_{max}$<5 newtons.

2. A composition according to claim 1, wherein said attachment angle $\alpha$ is greater than or equal to 90°, and the maximum detachment force $F_{max}$ is less than 2 newtons.

3. A composition according to claim 1, wherein said attachment angle $\alpha$ is greater than 50°.

4. A composition according to claim 1, wherein said at least one film-forming polymer is present in an amount ranging from 0.05% to 20% by weight, relative to the total weight of the composition.

5. A composition according to claim 4, wherein said at least one film-forming polymer is present in an amount ranging from 0.1% to 15% by weight, relative to the total weight of the composition.

6. A composition according to claim 5, wherein said at least one film-forming polymer is present in an amount ranging from 0.25% to 10% by weight, relative to the total weight of the composition.

7. A composition according to claim 1, wherein said cosmetically acceptable medium comprises a medium chosen from water, at least one cosmetically acceptable solvent, and water and at least one cosmetically acceptable solvent.

8. A composition according to claim 7, wherein said cosmetically acceptable solvent is chosen from alcohols.

9. A composition according to claim 8, wherein said alcohols are chosen from $C_1$–$C_4$ alcohols.

10. A composition according to claim 9, wherein said $C_1$–$C_4$ alcohols are chosen from ethanol and isopropanol.

11. A composition according to claim 10, wherein said alcohols are ethanol.

12. A composition according to claim 1 further comprising at least one additive chosen from thickeners, anionic, nonionic, cationic and amphoteric surfactants, fragrances, preserving agents, sunscreens, proteins, vitamins, provitamins, non-fixing anionic, cationic, nonionic and amphoteric polymers, mineral, plant and synthetic oils, waxes, ceramides, and pseudoceramides.

13. A spray, a lacquer, a mousse, a cream, a gel, an emulsion, a lotion or a wax comprising at least one film-forming polymer, in a cosmetically acceptable medium, wherein said at least one film-forming polymer has a mechanical profile, measured in an aqueous-alcoholic medium comprising 20% by volume, relative to the total volume of said aqueous-alcoholic medium, of ethanol, defined by at least:

(i) an attachment angle α of greater than 47°, and (ii) if α is greater than or equal to 90°, a maximum detachment force $F_{max}$<5 newtons.

14. An aerosol device comprising at least one film-forming polymer, wherein said at least one film-forming polymer has a mechanical profile, measured in an aqueous-alcoholic medium comprising 20% by volume, relative to the total volume of said aqueous-alcoholic medium, of ethanol, defined by at least:

(i) an attachment angle α of greater than 47°, and (ii) if α is greater than or equal to 90°, a maximum detachment force $F_{max}$<5 newtons.

15. A process for fixing or styling the hairstyle, comprising applying to hair an effective amount of a composition comprising at least one film-forming polymer, in a cosmetically acceptable medium, wherein said at least one film-forming polymer has a mechanical profile, measured in an aqueous-alcoholic medium comprising 20% by volume, relative to the total volume of said aqueous-alcoholic medium, of ethanol, defined by at least:

(i) an attachment angle α of greater than 47°, and (ii) if α is greater than or equal to 90°, a maximum detachment force $F_{max}$<5 newtons.

16. A process for manufacturing at least one cosmetic product comprising including in said product at least one film-forming polymer, wherein said at least one film-forming polymer has a mechanical profile, measured in an aqueous-alcoholic medium comprising 20% by volume, relative to the total volume of said aqueous-alcoholic medium, of ethanol, defined by at least:

(i) an attachment angle α of greater than 47°, and (ii) if α is greater than or equal to 90°, a maximum detachment force $F_{max}$<5 newtons.

* * * * *